(12) United States Patent
Li et al.

(10) Patent No.: US 7,742,177 B2
(45) Date of Patent: Jun. 22, 2010

(54) NOISE-REDUCTION METROLOGY MODELS

(75) Inventors: Shifang Li, Pleasanton, CA (US); Yu Liu, Sunnyvale, CA (US)

(73) Assignee: Tokyo Electron Limited, Tokyo (JP)

( * ) Notice: Subject to any disclaimer, the term of this patent is extended or adjusted under 35 U.S.C. 154(b) by 284 days.

(21) Appl. No.: 12/018,028

(22) Filed: Jan. 22, 2008

(65) Prior Publication Data
US 2009/0187383 A1    Jul. 23, 2009

(51) Int. Cl.
*G01B 11/14* (2006.01)

(52) U.S. Cl. .................................................. 356/625

(58) Field of Classification Search ............... 356/614, 356/625
See application file for complete search history.

(56) References Cited
U.S. PATENT DOCUMENTS
5,340,992 A * 8/1994 Matsugu et al. ............. 250/548
* cited by examiner

*Primary Examiner*—Roy Punnoose

(57) ABSTRACT

The invention can provide apparatus and methods for processing wafers using Noise-Reduction (N-R) metrology models that can be used in Double-Patterning (D-P) processing sequences, Double-Exposure (D-E) processing sequences, or other processing sequences.

19 Claims, 5 Drawing Sheets

500

NOISE-REDUCTION METROLOGY MODELS

CROSS-REFERENCE TO RELATED APPLICATIONS

This application is related to co-pending published U.S. Patent Application Publication No. 2007/0070211260 A1, entitled "WEIGHTING FUNCTION TO ENHANCE MEASURED DIFFRACTION SIGNALS IN OPTICAL METROLOGY". The contents of this publication is herein incorporated by reference in its entirety.

BACKGROUND OF THE INVENTION

1. Field of the Invention

The present invention relates to optical metrology, and more particularly to improving the optical metrology precision and procedures applying noise reduction to the data.

2. Description of the Related Art

Optical metrology involves directing an incident beam at a feature on a wafer, measuring the resulting diffraction signal, and analyzing the measured diffraction signal to determine various characteristics of the feature. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

With increased requirement on measurement precision, the measured diffraction signal may be relatively weak and not provide enough signal-to-noise (S/N) ratio. For example, the measured diffraction signal may include noise related to the hardware used to obtain the measured diffraction signal and to the feature being measured. The noise in the measured diffraction signal may decrease the precision and accuracy of the optical metrology process.

SUMMARY OF THE INVENTION

The invention provides apparatus and methods for processing wafers in real-time using Noise-Reduction Metrology (NRM) models that can be used in Double-Patterning (D-P) processing sequences, Double-Exposure (D-E) processing sequences, or other processing sequences. Noise data and noise-related measurement data can be suppressed with the NRM method to improve the modeling precision and accuracy in both real time integrated optical metrology and standalone optical metrology.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
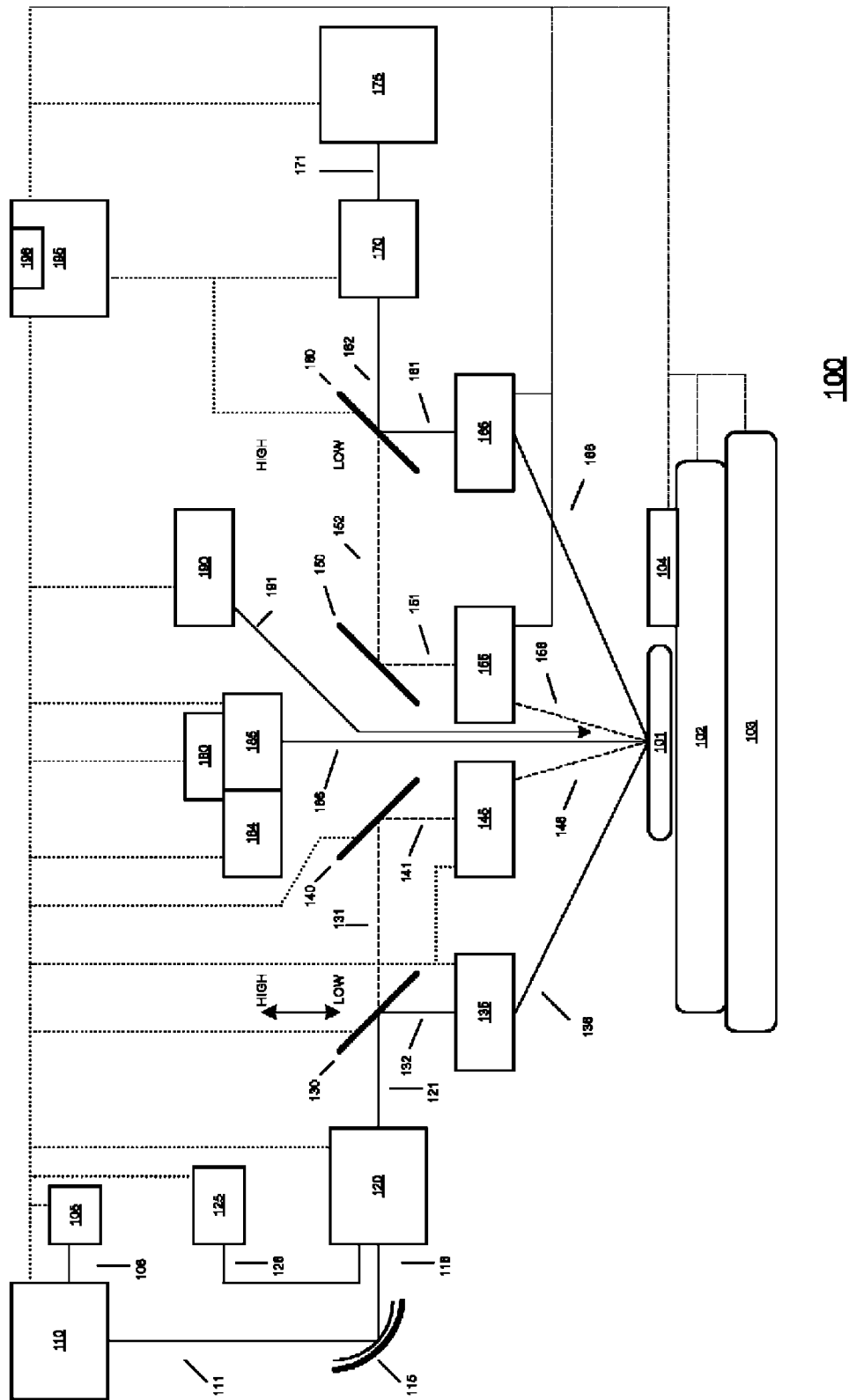
FIG. 1 depicts an exemplary optical metrology system in accordance with embodiments of the invention.

The invention can provide apparatus and methods for processing wafers using Noise-Reduction Metrology (NRM) models that can be used in real-time and non-real-time processing sequences that can include Double-Patterning (D-P) processing sequences, Double-Exposure (D-E) processing sequences, or other multi-step processing sequences. The D-P processing sequences can include one or more lithography-related procedures, one or more scanner-related procedures, one or more etch-related procedures, one or more deposition-related procedures, one or more measurement-related procedures, or one or more inspection-related procedures, or any combination thereof.

One or more multi-dimensional evaluation structures having one or more identifiable features can be provided at various locations on a wafer and can be used to align D-P layers and/or verify D-P procedures. For example, the evaluation structure can have two-dimensional or three-dimensional profiles and can include a grating or a repeating structure, and the features can include substructures such as footings, T-toppings, notches, and rounded tops. Wafers can have wafer data associated with them, and the wafer data can include real-time and historical data. In addition, the wafer can have other data associated with them, and the other data can include D-P pattern data, alignment data, overlay data, confidence data and/or risk data for one or more of the D-P patterns and/or sites, site ranking data, transferring sequence data, or process-related data, or evaluation/verification-related data, or any combination thereof. The data associated with D-P wafers can include data that can be used to establish how to align D-P layers. D-P processing sequences can also be established for each D-P wafer: In addition, the noise reduction can be used for many other applications.

In some examples, the wafers can have other layers deposited on them by a previous process or an external system, and the D-P sequences can include one or more lithography-related procedures, one or more scanner-related procedures, one or more evaluation procedures, and one or more etch-related procedures. For example, multi-step processing sequences can be established based on the number of wafers that require lithography-related processing, the number of wafers that require scanner-related processing, the number of available processing elements, the number of wafers that require evaluation, the number of available evaluation elements, and the loading data for one or more of the subsystems.

As structure sizes decrease below the 65 nm node, accurate processing and/or measurement data becomes more important and more difficult to obtain. N-R procedures can be used to more accurately process and/or measure these ultra-small devices and structures. The data from a D-P procedure can be compared with the accuracy, warning, and/or error limits, when a limit is exceeded, an alarm can be generated indicating a processing problem, and real-time correction procedures can be performed.

FIG. 1 shows an exemplary block diagram of an optical metrology system in accordance with embodiments of the invention. In the illustrated embodiment, an optical metrology system 100 can comprise a platform subsystem 103, an alignment subsystem 102 coupled to the platform subsystem 103, an alignment sensor 104 coupled to the alignment subsystem 102, and these subsystems can be configured to align the wafer 101. One or more optical outputs 106 from the lamp subsystem 105 can be transmitted to an illuminator subsystem 110. One or more optical beams 111 can be sent from the illuminator subsystem 110 to a selector subsystem 115. The selector subsystem 115 can provide one or more optical beams 116 to a beam generator subsystem 120. In addition, a reference subsystem 125 can provide one or more reference beams to and/or exchange data with the beam generator subsystem 120 using path 126.

The optical metrology system 100 can comprise a first selectable reflection subsystem 130 that can be used to direct one or more outputs 121 from the beam generator subsystem 120 as first outputs 131 when operating in a first mode "HIGH" or as second outputs 132 when operating in a second mode "LOW". When the first selectable reflection subsystem 130 is operating in the first mode "HIGH", one or more of the outputs 131 from the first selectable reflection subsystem 130 can be directed to a first reflection subsystem 140, and one or more outputs 141 from the first reflection subsystem 140 can be directed to a high angle focusing subsystem 145, When the first selectable reflection subsystem 130 is operating in the second mode "LOW", one or more of the outputs 132 from the first selectable reflection subsystem 130 can be directed to a low angle focusing subsystem 135. Alternatively, other modes may be used and other configurations may be used.

When the metrology system 100 is operating in the first mode "HIGH", one or more of the outputs 146 from the high angle focusing subsystem 145 can be directed to the wafer 101. For example, a high angle of incidence can be used. When the metrology system 100 is operating in the second mode "LOW", one or more of the outputs 136 from the low angle focusing subsystem 135 can be directed to the wafer 101. For example, a low angle of incidence can be used. Alternatively, other modes may be used and other configurations may be used.

The optical metrology system 100 can comprise a high angle collection subsystem 155, a low angle collection subsystem 165, a second reflection subsystem 150, and a second selectable reflection subsystem 160.

When the metrology system 100 is operating in the first mode "HIGH", one or more of the outputs 156 from the wafer 101 can be directed to the high angle collection subsystem 155. For example, a high angle of incidence can be used. In addition, the high angle collection subsystem 155 can process the outputs 156 obtained from the wafer 101 and high angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "HIGH" the outputs 152 from the second reflection subsystem 150 can be directed to the analyzer subsystem 170. For example, one or more blocking elements can be moved allowing the outputs 152 from the second reflection subsystem 150 to pass through the second selectable reflection subsystem 160 with a minimum amount of loss.

When the metrology system 100 is operating in the second mode "LOW", one or more of the outputs 166 from the wafer 101 can be directed to the low angle collection subsystem 165. For example, a low angle of incidence can be used. In addition, the low angle collection subsystem 165 can process the outputs 166 obtained from the wafer 101 and low angle collection subsystem 165 can provide outputs 161 to the second selectable reflection subsystem 160. When the second selectable reflection subsystem 160 is operating in the second mode "LOW", the outputs 162 from the second selectable reflection subsystem 160 can be directed to the analyzer subsystem 170.

When the metrology system 100 is operating in the first mode "HIGH", high incident angle data from the wafer 101 can be analyzed using the analyzer subsystem 170, and when the metrology system 100 is operating in the second mode "LOW", low incident angle data from the wafer 101 can be analyzed using the analyzer subsystem 170.

Metrology system 100 can include one or more measurement subsystems 175. One or more of the measurement subsystems 175 can include one or more spectrometers. For example, the spectrometers can operate from the Deep-Ultra-Violet to the visible regions of the spectrum.

The metrology system 100 can include one or more camera subsystems 180, one or more illumination and imaging subsystems 185 coupled to one or more of the camera subsystems 180. In addition, the metrology system 100 can also include one or more illuminator subsystems 184 that can be coupled to one or more of the imaging subsystems 185.

In some embodiments, the metrology system 100 can include one or more auto-focusing subsystems 190 that can be coupled 191 to the wafer 101. Alternatively, other focusing techniques may be used.

One or more of the controllers (not shown) in one or more of the subsystems (105, 110, 115, 120, 125, 130, 135, 140, 145, 150, 155, 160, 165, 170, 175, 180, 185 and 190) can be used when performing real-time or non-real-time N-R procedures. A controller can receive real-time or non-real-time data to update subsystem, processing element, process, recipe, profile, image, pattern, and/or model data. One or more of the subsystems (105, 110, 115, 120, 125, 130, 135, 140, 145, 150, 155, 160, 165, 170, 175, 180, 185 and 190) can exchange data using one or more Semiconductor Equipment Communications Standard (SECS) messages, can read and/or remove information, can feed forward, and/or can feedback the information, and/or can send information as a SECS message.

Those skilled in the art will recognize that one or more of the subsystems (105, 110, 115, 120, 125, 130, 135, 140, 145, 150, 155, 160, 165, 170, 175, 180, 185 and 190) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. One or more of the subsystems (105, 110, 115, 120, 125, 130, 135, 140, 145, 150, 155, 160, 165, 170, 175, 180, 185 and 190) can include the means for reading data and/or instructions from a computer readable medium and can comprise the means for writing data and/or instructions to a computer readable medium. The metrology system 100 can perform a portion of or all of the processing steps of the invention in response to the computers/processors in the processing system executing one or more sequences of one or more instructions contained in a memory and/or received using a computer-readable medium. Such instructions may be received from another computer, a computer readable medium, or a network connection. In addition, one or more of the subsystems (105, 110, 115, 120, 125, 130, 135, 140, 145, 150, 155, 160, 165, 170, 175, 180, 185 and 190) can comprise control applications, Graphical User Interface (GUI) components, and/or database components. For example, the control applications can include Advanced Process Control (APC) applications, Fault Detection and Classification (FDC), and/or Run-to-Run (R2R) applications. In some embodiments, APC applications, FDC applications, and/or R2R applications can be performed using Noise-Reduction (N-R) procedures.

Output data and/or messages from N-R can be used in subsequent procedures to optimize the process accuracy and precision. Data can be passed to D-P procedures in real-time as real-time variable parameters, overriding current recipe or model default values and narrowing the search space for resolving accurate results. Real-time sensor noise data can be used with a library-based system, or regression-based system, or any combination thereof to optimize a D-P procedure.

In some embodiments, the metrology system 100 can include integrated Optical Digital Profilometry (iODP) elements (not shown), and iODP elements/systems are available from Timbre Technologies Inc. (a TEL company). Alternatively, other metrology systems may be used. For example, iODP techniques can be used to obtain real-time data that can include critical dimension (CD) data, gate structure data, and thickness data, and the wavelength ranges for the iODP data can range from less than approximately 200 nm to greater than approximately 900 nm. Exemplary iODP elements can include Optical Digital Profilometry (ODP) Profiler Library elements, Profiler Application Server (PAS) elements, and ODP Profiler Software elements. The ODP Profiler Library elements can comprise application specific database elements of optical spectra and its corresponding semiconductor profiles, critical dimensions (CDs), and film thicknesses. The PAS elements can comprise at least one computer that connects with optical hardware and computer network. The PAS elements can be configured to provide the data communication, ODP library operation, measurement process, results generation, results analysis, and results output. The ODP Profiler Software elements can include the software installed on PAS elements to manage measurement recipe, ODP Profiler library elements, ODP Profiler data, ODP Profiler search/match results, ODP Profiler calculation/analysis results, data communication, and PAS interface to various metrology elements and computer network.

The metrology system 100 can use polarizing reflectometry, spectroscopic ellipsometry, spectroscopic reflectometry, or other optical measurement techniques to measure accurate device profiles, accurate CDs, and multiple layer film thickness of a wafer. The integrated metrology process (iODP) can be executed as an integrated process in an integrated group of subsystems. In addition, the integrated process eliminates the need to break the wafer for performing the analyses or waiting for long periods for data from external systems. iODP techniques can be used with the existing thin film metrology systems for inline profile and critical dimension (CD) measurement, and can be integrated with TEL processing systems and/or lithography systems to provide real-time process monitoring and control.

An exemplary optical metrology system is described in U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference.

Simulated diffraction signals can be generated by applying Maxwell's equations and using a numerical analysis technique to solve Maxwell's equations. For example, various numerical analysis techniques, including variations of rigorous coupled wave analysis (RCWA), can be used with multi-layer structures. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

An alternative procedure for generating a library of simulated-diffraction signals can include using a machine learning system (MLS). Prior to generating the library of simulated-diffraction signals, the MLS is trained using known input and output data. For example, the MLS may be trained with a subset of the D-P library data. In one exemplary embodiment, simulated diffraction signals can be generated using a MLS employing a machine learning algorithm, such as back-propagation, radial basis function, support vector, kernel regression, and the like. For a more detailed description of machine learning systems and algorithms, see "U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

When a regression-based process is used, a measured diffraction signal measured off the patterned structure can be compared to simulated diffraction signals. The simulated diffraction signals can be iteratively generated based on sets of profile parameters, to get a convergence value for the set of profile parameters that generates the closest match simulated diffraction signal compared to the measured diffraction signal. For a more detailed description of a regression-based process, see U.S. Pat. No. 6,785,638, titled METHOD AND SYSTEM OF DYNAMIC LEARNING THROUGH A REGRESSION-BASED LIBRARY GENERATION PROCESS, issued on Aug. 31, 2004, which is incorporated herein by reference in its entirety.

When a library-based process is used, an optical metrology data library can be generated. For example, a D-P evaluation library can comprise simulated and/or measured optical signals and corresponding set of profile parameters. A detailed description of generating optical metrology data such as a library of simulated diffraction signals and corresponding set of profile parameters is described in U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference. The regression-based and/or the library-based process can include N-R procedures.

One or more of the D-P procedures can be context dependent and can include data collection, control, and analysis strategies to provide real-time processing, and dynamic context matching allows for custom configuration. One or more of the N-R procedures can include intervention and/or judgment rules can be executed whenever a matching context is encountered.

In various embodiments, one or more of the subsystems (105, 110, 115, 120, 125, 130, 135, 140, 145, 150, 155, 160, 165, 170, 175, 180, 185 and 190) can perform evaluation procedures, inspection procedures, temperature control procedures, measurement procedures, alignment procedures, verification procedures, and/or storage procedures on one or more wafers. For example, wafer data that can include wafer temperature, wafer thickness, wafer curvature, layer thickness, wafer uniformity, pattern data, damage data, or particle data, or any combination thereof. In addition, controller 195 can determine if the wafer has been processed correctly or if a rework procedure is required.

N-R procedures can be used to more accurately measure isolated and/or nested structures at different sites. For example, pattern layer and/or wafer thickness data can be different near isolated and/or nested structures, and wafer thickness data can be different near open areas and/or trench array areas. The metrology system 100 can use new noise-reduced data for isolated and/or nested structures to update and/or optimize a process recipe and/or process time.

Metrology system 100 data can include measured, predicted, and/or simulated data associated with D-P patterns or structures, and the data can be stored using processing, wafer, lot, recipe, site, or wafer location data. the data can include variables associated with patterned structure profile, metrology device type and associated variables, and ranges used for the variables floated in the modeling and values of variables that were fixed in the modeling. The library data may include fixed and/or variable profile parameters (such as CD, sidewall angle, refractive index (n) data and extinction coefficient (k) data), and/or metrology device parameters (such as wavelengths, angle of incidence, and/or azimuth angle). For example, context and/or identification information such as sensor ID, site ID, wafer ID, slot ID, lot ID, recipe, state, and patterned structure ID may be used for organizing and indexing data.

Controller 195 can include coupling means 196 that can be used to couple the metrology system 100 to other systems in a factory environment. In some examples, controller 195 may be configured to use factory level intervention and/or judgment rules to determine which processes are monitored and which data can be used. In addition, factory level intervention and/or judgment rules can be used to determine how to manage the data when a process can be changed, paused, and/or stopped. In addition, controller 195 can provide configuration information and update information.

In some embodiments, an N-R procedure can be performed using sensor data from one or more optical sensors. When N-R procedures are performed, data N-R-related data can be obtained from other components in the metrology system 100. N-R-related data can be used to determine accuracy problems, confidence values, and risk factors during a D-P procedure. For example, when a target structure is created on a first wafer, first N-R-related data can be obtained for the first wafer using a first sensor, and when the target structure is created on a second wafer, second N-R-related data can be obtained for the second wafer using the first sensor, and one or more matching criteria can be determined using the N-R-related data. In addition, N-R procedures can be performed using one or more "golden wafers" that can be stored and used periodically to verify the performance of one or more of the chambers. Furthermore, one or more reference chips associated with a measurement, evaluation, and/or inspection chamber may be used during sensor calibration and/or matching.

For example, N-R-related data can include pattern data, alignment data, overlay data, material data, critical dimension (CD) data, sidewall angle (SWA) data, structure data, or thickness data, or any combination thereof. In addition, sensor-matching procedures can be updated using the first real-time sensor-matching data when updating rules are not violated.

Verified NRM data for a D-P procedure can be obtained by performing the D-P procedure using a "golden" metrology chamber, can be historical data that is stored in a library, can be obtained by performing a verified D-E procedure, can be obtained from the factory system, can be simulation data, and can be predicted data. Wafer 101 can be, for example, a semiconductor substrate, a work piece, or a liquid crystal display (LCD).

Figure 2:
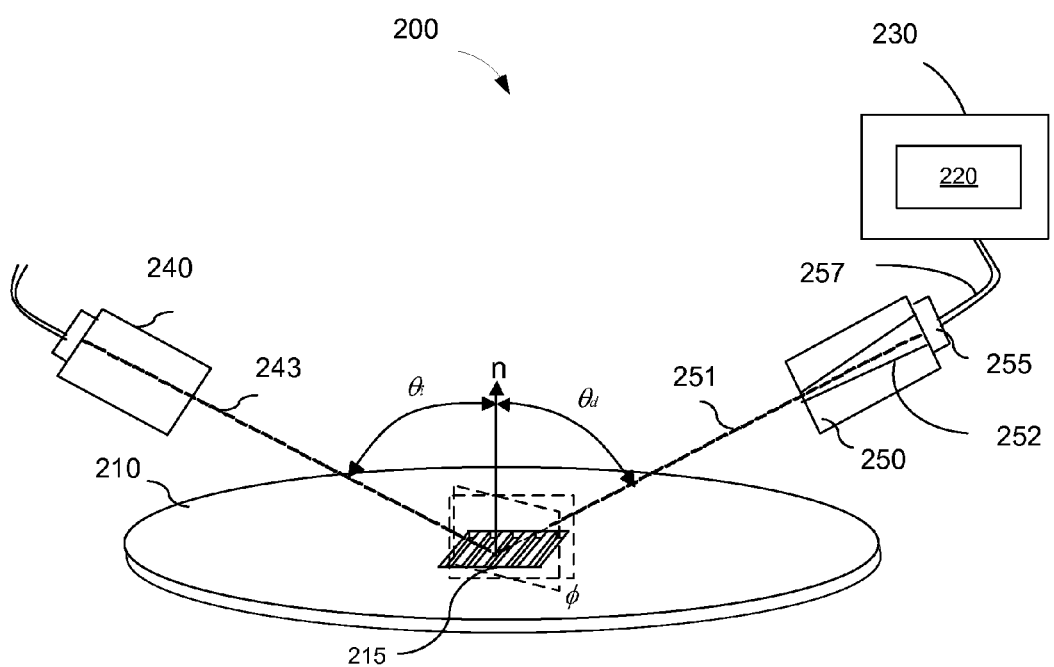
FIG. 2 depicts another exemplary optical metrology system in accordance with embodiments of the invention.

FIG. 2 depicts an exemplary optical metrology system in accordance with embodiments of the invention. In the illustrated embodiment, an optical metrology system 200 is shown that can be used to examine and analyze a structure formed on a wafer. Alternatively, other configurations may be used. The illustrated optical metrology system 200 can be used to determine the profile of a target structure 215 formed on wafer 210. The target structure 215 can be formed in test areas on wafer 210, such as adjacent to a device formed on wafer 210. In other embodiments, target structure 215 can be formed in an area of the device that does not interfere with the operation of the device or along scribe lines on wafer 210.

The illustrated optical metrology system 200 can include a photometric device with a beam source 240 and a beam receiver 250. Target structure 215 is illuminated by an incident beam 243 from beam source 240. In the illustrated exemplary embodiment, incident beam 243 is directed onto target structure 215 at an angle of incidence $\theta_i$ with respect to normal n and an azimuth angle $\phi$ i.e., the angle between the incident plane of source beam and the direction of the periodicity of target structure 215). Measurement beam 251 leaves at an angle of $\theta_d$ with respect to normal {right arrow over (n)} and is received by beam receiver 250. The beam sensor 255 in the beam receiver can convert the measurement beam 251 into measurement data 257. In addition, the measurement beam 251 can have a beam width 252 at the beam sensor 255.

To determine the profile of target structure 215, optical metrology system 200 includes one or more controller/servers 230 that can be configured to receive measurement data 257 and analyze the measurement data 257. For example, measurement data 257 can include one or more of the measured diffraction signals with unwanted noise in the signal. The profile of target structure 215 can then be determined using a library-based optical metrology process or a regression-based optical metrology process, to the precision level limited by unwanted noise in the signal. When the unwanted noise in the signal is suppressed by the NRM, the measurement precision of the profile of target structure is improved. In additional embodiments, other linear or non-linear profile extraction techniques may be used.

It should be recognized that optical metrology system 200 can be used to examine and analyze various types of structures other than target structures 215, such as a thin film layer, features of the actual device, and the like. Additionally, a library-based optical metrology process or a regression-based optical metrology process can be used to determine various characteristics other than profile, such as the thickness of a thin film layer, or defects in structures and/or thin film layers, or process parameters. A detailed description of generating optical metrology data using dispersion related techniques is described in U.S. patent application Ser. No. 11/858,882, entitled "Determining Profile Parameters of a Structure Formed on a Semiconductor Wafer Using a Dispersion Function Relating Process Parameter to Dispersion", by Li, et al., filed on Sep. 20, 2007, and U.S. patent application Ser. No. 11/859,669, entitled "Automated Process Control of a Fabrication Tool Using a Dispersion Function Relating Process Parameter to Dispersion", by Li, et al., filed on Sep. 21, 2007, both of which are incorporated herein by reference in their entirety.

In some library-based optical metrology procedures, the measured diffraction signal can be compared to a library of simulated diffraction signals, and each simulated diffraction signal in the library can be associated with an optical metrology model of the structure. When a match is made between the measured diffraction signal and one of the simulated diffraction signals in the library or when the difference of the measured diffraction signal and one of the simulated diffraction signals is within a preset or matching criterion, the optical metrology model associated with the matching simulated diffraction signal can be used to represent the feature. The matching simulated diffraction signal and/or optical metrology model can then be compared to product requirements to determine whether or not the feature has been fabricated according to specifications. For example, after obtaining measured diffraction data, controller/server 230 can be used to compare the measured diffraction signal to the simulated diffraction signal stored in a library. In addition, the data in library 220 can include optical metrology model data, and when a match is made between measured data and simulated data in library 220, the optical metrology model data associated with the matching condition can be used to characterize the target structure 215.

The optical metrology model data stored in library 220 can be generated by characterizing the profile of target structure 215 using a set of profile parameters, then varying the set of profile parameters to generate optical metrology models of varying shapes and dimensions. The process of characterizing a profile using a set of profile parameters can be referred to as parameterizing.

Figure 3A:
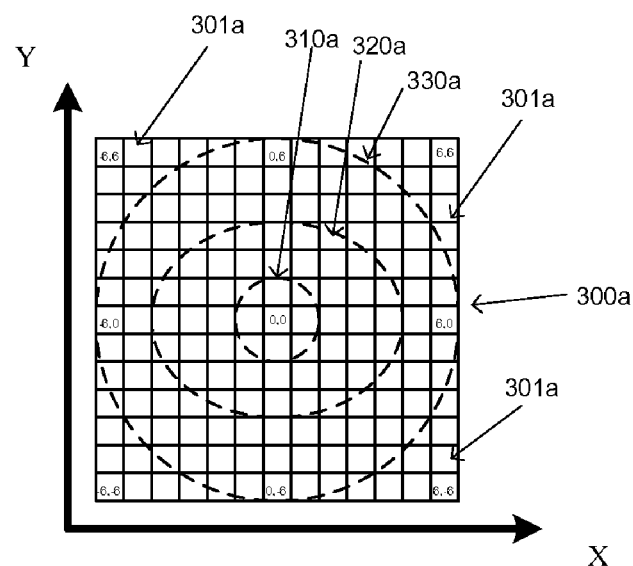
FIGS. 3a and 3b show exemplary pixel arrays in accordance with embodiments of the invention.
Figure 3B:
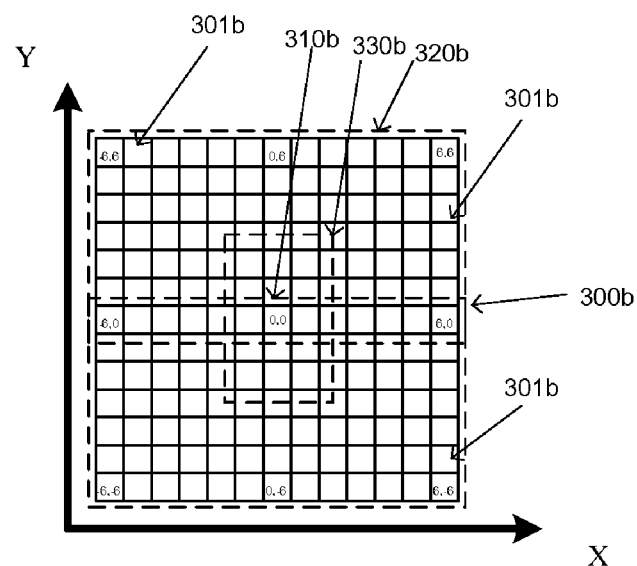

FIGS. 3a and 3b show exemplary pixel arrays in accordance with embodiments of the invention. In FIG. 3a, a first two-dimensional pixel array 300a is shown that includes a plurality of pixels 301a. The first and second two-dimensional pixel arrays (300a and 300b) can be used to illustrate a portion of the pixels (sensing elements) in the collection subsystems (155 and 165, FIG. 1) and/or the beam sensor (255, FIG. 2). Alternatively, different configurations and other sensors may be used.

In FIG. 3a, a thirteen-by-thirteen [13×13] pixel array 300a is shown that comprises one hundred sixty nine [169] pixels 301a. Alternatively, other pixel arrays may be used. The center pixel is labeled (0,0), the top-left side corner pixel is labeled (−6,6), the top-right side corner pixel is labeled (6,6), the bottom-left side corner pixel is labeled (−6,−6), and the bottom-right side corner pixel is labeled (6,−6). The labeling indicates the position of the pixel relative to the center pixel. Alternatively, different labeling schemes may be used. The first circular pattern of pixels 310 is shown that can be used to obtain a first set of measured diffraction signals. An elliptical pattern 320a of pixels 301a are shown that can be used to obtain second set of measured diffraction signals. A second circular pattern 330a of pixels is shown that can be used to obtain third set of measured diffraction signals. In various embodiments, measured diffraction signals can be obtained using any number of the pixels 301a. In various example, one or more first measurements can be made using the first number of pixels in the circular pattern 310a of pixels 301a, one or more second measurements can be made using the second number of pixels in the elliptical pattern 320a of pixels 301a, and one or more third measurements can be made using the third number of pixels in the second circular pattern 330a of pixels 301a, In FIG. 3b, another thirteen-by-thirteen [13×13] pixel array 300b is shown that comprises one hundred sixty nine [169] pixels 301b. Alternatively, other pixel arrays may be used. The center pixel is labeled (0,0), the top-left side corner pixel is labeled (−6,6), the top-right side corner pixel is labeled (6,6), the bottom-left side corner pixel is labeled (−6,−6), and the bottom-right side corner pixel is labeled (6,−6). The labeling indicates the position of the pixel relative to the center pixel. Alternatively, different labeling schemes may be used. A first rectangular pattern 310b of pixels 301b are shown that can be used to obtain a first set of measured diffraction signals. A square pattern 320b of pixels 301b are shown that can be used to obtain a second set of measured diffraction signals. A second rectangular pattern 330b of pixels is shown that can be used to obtain a third set of measured diffraction signals. In various embodiments, measured diffraction signals can be obtained using any number of the pixels 301b. In various example, one or more first measurements can be made using the first number of pixels in the rectangular pattern 310b of pixels 301b, one or more second measurements can be made using the second number of pixels in the square pattern 320b of pixels 301b, and one or more third measurements can be made using the third number of pixels in the second rectangular pattern 330b of pixels 301b.

In some measurement procedures (e.g., in a spectrometer), the signal at any pixel 301 is not independent, and adjacent pixels can detect similar signals at the same wavelength. A number of mathematical techniques have been used by different manufacturers with varying degrees of success. For example, the mathematical techniques can include moving box averaging, FFT, frequency filtering, and weighted averaging. The inventors believe that these methods have spectral resolution problems and/or data integrity problems, and believe that these problems can be identified by checking the spectral difference before and after data processing.

The convolution algorithm is one of the experimental data post process methods, and can be used to convolute a certain number of adjacent data point to reduce the noise in measurement data, i.e.

$$S(i) = \frac{\sum_{j=-m_1}^{m_2} s(i+j) \cdot W_j}{\sum_{j=-m_1}^{m_2} W_j}$$

where s(i) is the diffraction signal before processing, and S(i) is the signal after processing, and $(m_1, m_2)$ are parameters and $W_j$ is the convolution kernel function. The parameter $m_1$ illustrates the number of pixels to the left of the center pixel (0,0) shown in FIGS. 3a and 3b, and $m_2$ illustrates the number of pixels to the right of the center pixel (0,0) shown in FIGS. 3a and 3b, and are pre-determined parameters of the algorithm. The determination criteria includes the ratio of noise suppression, pixel separation to system resolution ratio, and for best effect, sometimes the user may desire to adjust per measurement target structure by examining the speed of signal variation.

The moving box average can be regarded as a special case, where the kernel function is a "gate" function, so that, $$S(i) = \frac{1}{m_1 + m_2} \sum_{j=-m_1}^{m_2} s(i+j)$$

where $m_1$ and $m_2$ have similar meanings and determining criteria as prior method.

When frequency filtering is used, the assumption is that the signal cannot vary from one pixel to adjacent pixels randomly, that is there should be no or less high frequency component, thus some or all of the high frequency components are contribution from noise, and are removed. The algorithm is $$\tilde{s}(k)=\mathrm{DFT}(s(j)),\ \tilde{S}(k)=F(k)\cdot(k),\ \text{then}\ S(i)=\mathrm{DFT}(\tilde{S}(k))/N$$

where DFT means digitized Fourier transfer, N is the normalization constant to count forward and inverse DFT, and F(k) is the filter function, its form can be user selected, often used filter functions are cut-off or Guassian, where the symbols with ~ means the symbols are in the frequency domain. Here is filter function at its parameters is pre-determined by design. The actual selection and criteria includes the ratio of noise suppression, pixel separation to system resolution ratio, and for best effect, sometimes the user may desire to adjust per measurement target structure by examining the speed of signal variation.

Figure 4:
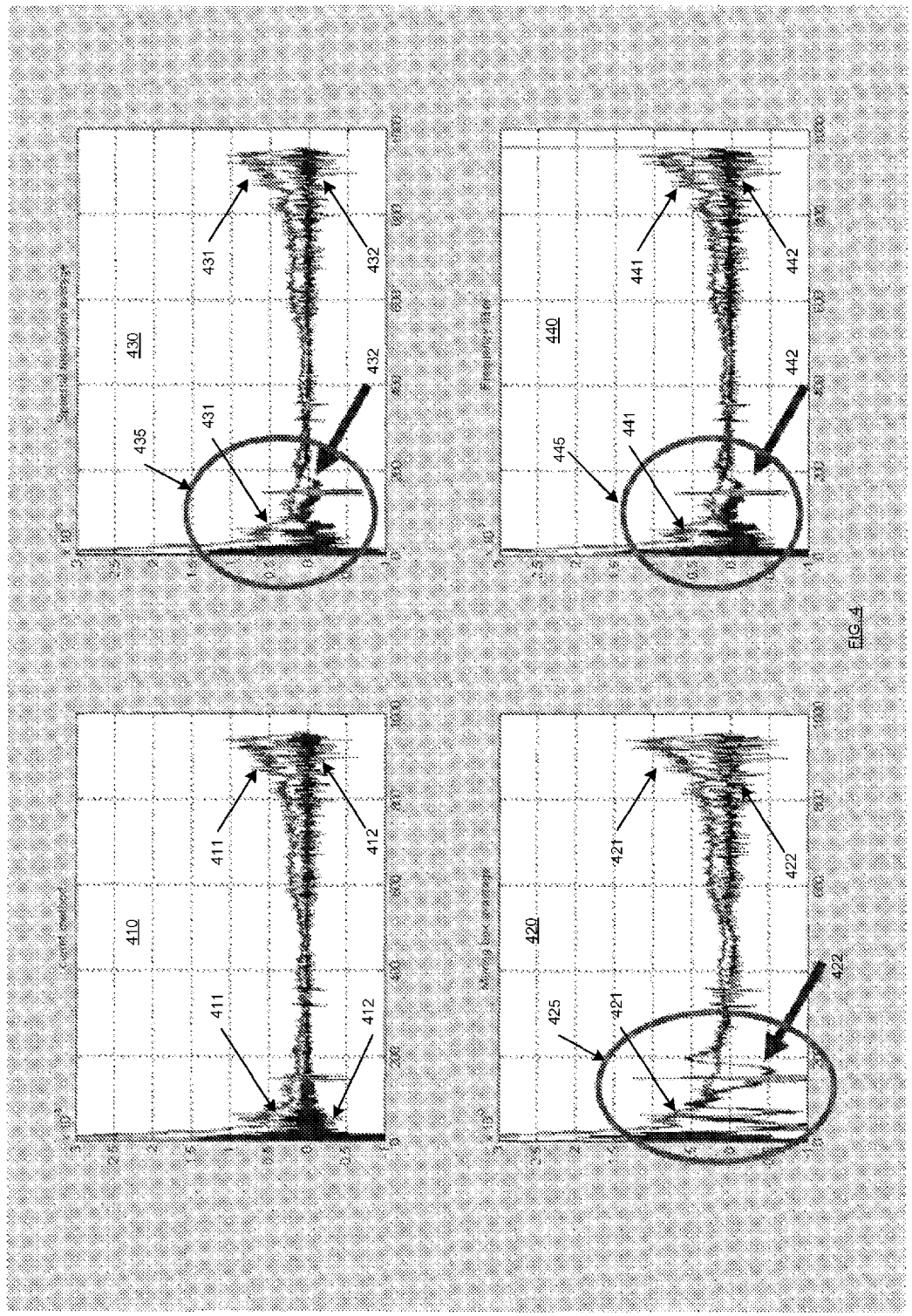
FIG. 4 illustrates exemplary graphs of experimental results in accordance with embodiments of the invention.

FIG. 4 illustrates exemplary graphs of experimental results in accordance with embodiments of the invention. In the illustrated graphs (410, 420, 430, and 440), the spectral differences are shown for four different processing techniques. If a first set of repeatable measurements (e.g. 30) were made in a perfect (noise-free) environment, the measurement data from the first set of measurements would be identical because noise was not present. When the first set of repeatable measurements (e.g. 30) are made in a non-perfect (noisy) environment, the measurement data from the first set of measurements is not identical because noise was present. When a first set of measurements are made in a non-perfect (noisy) environment, an average value can be calculated using the measurement data from the first set of measurements, and the average value can be used as a reference value that represents a best estimate of the "true" diffraction signal without noise. Then, noise reduction techniques can be applied to the 30 individual diffraction spectra. In graph 410, the signal deviation (3σ) of a first set of processed spectra (e.g., a first set of 30 measurements) is shown as 411, and the mean value of a number of differences (e.g. 30) between the spectra before the noise-reduction process and the spectra after noise-reduction process is shown as 412 for the current N-R method. In graph 420, the signal deviation (3σ) of a second set of processed spectra (e.g., a second set of 30 measurements) is shown as 421, and the mean value of a second number of differences (e.g. 30) between the spectra before the noise-reduction process and the spectra after noise-reduction process is shown as 422 for a Moving Box average method. In graph 430, the signal deviation (3σ) of a third set of processed spectra (e.g., a third set of 30 measurements) is shown as 431, and the mean value of a third number of differences (e.g. 30) between the spectra before the noise-reduction process and the spectra after noise-reduction process is shown as 432 for a "Spectral resolution average" method. In graph 440, the signal deviation (3σ) of a fourth set of processed spectra (e.g., a fourth set of 30 measurements) is shown as 441, and the mean value of a fourth number of differences (e.g. 30) between the spectra before the noise-reduction process and the spectra after noise-reduction process is shown as 442 for a "Frequency filter" method. The inventors believe that the difference curves (412, 422, 432, and 442) shown in the graphs (410, 420, 430, and 440) demonstrate the efficiency of the noise-removal process and demonstrate that the integrity of the signal is not changed by the noise-removal process. If the curves (412, 422, 432 and 442) are simply random varying around zero (like 412), the noise reduction process just removes the noise and the signal integrity remains unchanged. In contrast, if the curves (412, 422, 432 and 442) show systematic deviation from zero (like 411) we can see the structures inside circles (425, 435, and 445); the signal integrity is changed while the noise is reduced. In other words, all those prior methods sacrifice data integrity, as shown by the spectral shape differences between the graphs of FIG. 4. Since the differences are small, there is a slight risk that the final CD profile may change.

The new noise-reduction (N-R) procedures do not sacrifice data integrity and just remove the random/statistic noise component. The new noise-reduction algorithm assumes that the signal at adjacent pixels of the detector array change smoothly in the local range. Unlike the box averaging, the procedure assumes the signal is constant when m1≠m2, or varying linear when m1=m2. The new noise-reduction procedure allows the signal variation more complicated than linear change and still smoothly. This is true because pixel separation is designed so that the reflectivity of the samples does not change rapidly from pixel to pixel (otherwise, there will be significant measurement error). Furthermore, the spectrometer resolution is typically wider than the pixel separation, and this further smoothes the signal variation from pixel to pixel. The instrument typically also has other effects, such as numerical aperture (NA) integration, smoothes the spectra.

In the current noise-reduction procedures, also called basis function method, the local data points (pixels) are forced to follow a basis function, and the signal at a local point can be in the following format:

$$s(i)=a(i)\cdot b(i,p)+r(i)+n(i)$$

where a and p are parameters to be determined, b(..) is a pre-selected basis function, r(i) is the residual of real signal from basis function, and no is the noise to be suppressed. A simple basis function can, for example, be a polynomial $$b(i,p)=p(0)+p(1)\cdot i+p(2)\cdot i^2+\ldots$$

The parameters a(i) and p can be selected so that the basis function most closely represents the real signal locally, and r(i) is minimum. In some cases, a regression method can be used to minimize the residual r(i) by adjust the parameters of the basis function. For example, s(i) can be the actual reading from an instrument, and can contain some noise n(i), that can be approximated using an average value obtained from a large number of measurements. The term s(i)-n(i) can be identified as a real signal that would be obtained from an ideal instrument, which can operate without noise. In addition, the real signal s(i)-n(i) can vary over (i) and can be any shape. The invention as described herein uses a small range of this function versus time, so that the can be approximated by a basis function in this small range. A basis function can be a pre-selected function type (such as a polynomial) with parameters that can be adjusted to best represent the shape of the real signal in the small range. Furthermore, there is a difference between the real signal shape and the basis function can represent, and the difference is defined as the residual signal, r(i). The residual term is needed to make the equation mathematically correct, and in some embodiments, the residual term can be very small and can be ignored. The inventors have discovered that the residual r(i) is typically small at center of a set of points, and that a regression procedure can be performed for one or more of the data points. The noise-reduction procedures can be performed in real time. For example, the inventors have processed a spectral set with 1024 data points in approximately 15 milliseconds, each data point representing one diffraction signal.

Figure 5:
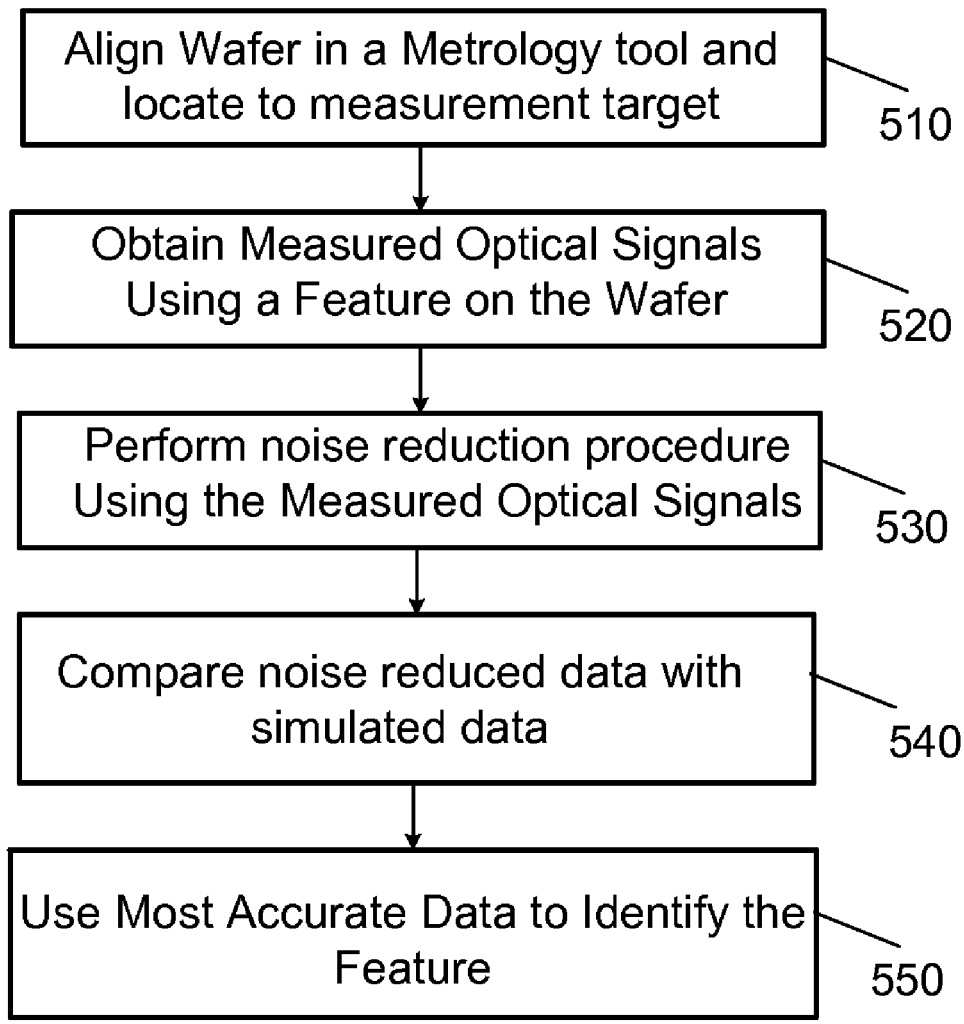
FIG. 5 illustrates an exemplary flow diagram for a Noise-Reduction (N-R) procedure in accordance with embodiments of the invention.

FIG. 5 illustrates an exemplary flow diagram for a Noise-Reduction (N-R) procedure in accordance with embodiments of the invention.

In 510, a wafer can be positioned in a metrology tool, and a measurement target can be identified on the wafer. The measurement target can include one or more evaluation structures and/or process-related features.

In 520, a first set of measured diffraction signals can be obtained for the wafer using one or more of the evaluation and/or process-related features.

In 530, one or more noise-reduction procedures can be performed and noise-reduced data can be obtained. The inventors believe the basis function method is the most efficient method for a noise-reduction procedure, and the basis function method has a minimum effect on data integrity when obtaining the desired noise suppression ratio. In some examples, a "Spectral resolution average" method, a Moving Box average method, or a "Frequency filter" method could also be used, but there is a higher risk on the data integrity of the noise-reduced data.

For example, Matlab code can be used to illustrate the basis function method of noise reduction procedure. In this exemplary Matlab code, the basis function is a $2^{nd}$ order polynomial and the variables $m_1$ and $m_2$ can be set equal to four and can be dependent upon the pre-selected per instrument resolution, the pixel separation and the order of the selected polynomial. The measured diffraction signals can be analyzed in a piecewise manner as illustrated below in the exemplary Matlab code as array y. In this exemplary code, the "for loop with index i" shown in the exemplary Matlab code illustrates that the center of each piece of measured data is at pixel i and the four pixels at each side are also used. The 9 points in each piece of measured data is fitted to a $2^{nd}$ order polynomial, $p(0)+p(1)*x+p(2)*x*x$, where $x=[-4,4]$. In addition, the residual $r(..)+n(..)$ can be minimized by adjusting $p(0)$, $p(1)$, and $p(2)$, and this can be done by calculating a matrix A as shown below in the exemplary code. The matrix can be the same for each selected piece of the measured data y. In one embodiment, a noise-reduction procedure can be performed using the following code.

```
m1 = -4, m2 = 4; %define parameters m1 and m2
% Pre-determine the matrix A for coefficient calculation
x = (m1:m2)';
A(1,1) = length(x);
A(1,2) = sum(x);        A(2,1) = A(1,2);
A(1,3) = sum(x.^2);     A(3,1) = A(1,3);    A(2,2) = A(1,3);
A(2,3) = sum(x.^3);     A(3,2) = A(2,3);
A(3,3) = sum(x.^4);
A = inv(A);
% Read in data and perform noise-reduction procedure
for jj = 1:MeasurementPoint
    Data = load('test'); %read in "raw" data and store in Data
    b = Data;
    n = length(Data);
    for i = (1-m1):(n-m2)
        y = Data((i+m1):(i+m2));
        X(1) = sum(y);
        temp = y.*x;        X(2) = sum(temp);
        temp = temp.*x;     X(3) = sum(temp);
        b(i) = A(1,:) * X';
    end
end
% in return, b is the noise-reduced data
```

In the illustrated embodiment, the commonly calculated matrix A can be pre-calculated before it is applied to each pixel of the "raw" measurement data—as shown in the "loop with index i", and can be applied to each measurement data set—as shown in the "loop with index jj". In this way, the calculation time can be decreased by a factor of 4-5. Other feature of the exemplary code is that for a giving pixel, only $a(i)*p(0)$ is needed, and other term like $a(i)*p(1)$, $a(i)*p(2)$ etc are not needed because the exemplary code assumes that the residual is typically small at center of a set of points y. In this way, the calculation time can be decreased by a factor up to 3.

In 540, the noise-reduced data can be compared to simulation data. The simulation data can be obtained from a library or by using a RCWA-like simulator, and the simulation data can have simulated accuracy data associated therewith.

In 550, the target structure can be identified. In some examples, the target structure can be identified using the first noise-reduced data when the noise-reduced data is more accurate than the simulated data, and the target structure can be identified using the simulation data when the first accuracy data is not more accurate than the simulated accuracy data. In other examples, the target structure can be identified using the first noise-reduced data when the first noise-reduced data is more accurate than the simulation data, and the target structure can be identified using the simulation data when the first noise-reduced data is not more accurate than the simulation data.

In some embodiments, another procedure can be performed for examining a structure formed on a semiconductor wafer using Noise-Reduced (N-R) metrology model, and the procedure can include the following steps: a) creating a Noise-Reduced (N-R) metrology model for the structure, the N-R metrology model comprising one or more profile parameters, which characterize one or more geometric characteristics of the structure, one or more process parameters, which characterize one or more process conditions for fabricating the structure, and one or more noise-related parameters, which characterize noise parameters associated with a measurement of the structure; b) generating a simulated N-R diffraction signal using the N-R metrology model and a value for the at least one of the process parameters and a value for at least one of the noise parameters, wherein N-R data is calculated using the value for the at least one of the process parameter and the N-R model; c) obtaining a measured diffraction signal for the structure; d) identifying the structure using the simulated N-R diffraction signal when the simulated N-R diffraction signal is more accurate than the measured diffraction signal; and e) creating a new N-R model when the simulated N-R diffraction signal is not more accurate than the measured diffraction signal.

When noise-reduction procedures are used, the metrology data obtained is more accurate than the data obtained using the prior art methods. In the illustrated graphs (410, 420, 430 and 440), the noise-reduction parameters ($m_1$ and $m_2$) of each data process is set in the way that all the 4 noise-reduction procedures obtain a noise reduction that is approximately equal. As mentioned above, the inventors believe that the new noise-reduction procedures remove random noise without changing the mean. In other word, the new noise-reduction procedures remove random noise minimum scarify data integrity. This is obvious when curves 412, 422, 432, and 442 are compared. Moreover, this is further validated by test the profile extracted from the spectra before and after noise-reduction procedure. As shown below, the extracted profiles are not changed while the precision improved significantly.

Testing was done by running 30 measurements before and after the noise-reduction procedure through ODP. As shown in the table below, the 3 sigma improves significantly (top CD (TCD) from 0.15 to 0.10), and the mean value stays the same (TCD from 33.40 to 33.42).

|  |  | TopCD | GratingThickness |
|---|---|---|---|
| 3sigma | Before | 0.15 | 0.22 |
| 3sigma | after | 0.10 | 0.14 |
| Average | Before | 33.40 | 112.53 |
| Average | after | 33.42 | 112.54 |

In N-R measurement procedures, library-based optical metrology techniques can be used, and the N-R measurement data can be compared to simulation data in a library. That is, the noise reduction procedure is simply applied to the measurement data, to remove the measurement noise and improve measurement precision. The procedure can apply to any single measurement, without any adjustment on the simulation signal such as RCWA and/or library spectra-regeneration algorithm and process.

Precision is an indication of how repeatable a measurement can be made. The ideal case is that of measuring a profile model parameter, such as CD, ten times and the measurements yield the exact same answer every time. Since there is always certain amount of variation from one measurement to another and noise in every measurement, precision values are typically reported in terms of multiples of the standard deviation of the repeated measurement ($\sigma$). Typically, a three-sigma, ($3\sigma$), where the values included in the stated range represent 99.7% of the data population. Alternatively, other statistical measures such as, $6\sigma$ that represent the range of the data population and the like may be employed as well.

For optical metrology measurements, static precision, dynamic precision, and/or long-term precision may be specified. Static precision refers to the variation in measured value when no movement of the wafer relative to the measurement optics occurs. This test typically represent the noise level of the measurement sensor head. Dynamic precision, also known as reproducibility, refers to the variation in measured value when the wafer is unloaded and reloaded between measurements. This is a test typically represent the overall system stability. Long-term precision refers to the variation in measured value over a relatively long period.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention. In addition, the noise-reduction approach can be applied to D-P, D-E, and other semiconductor applications. Furthermore, the noise reduction approach can be used for real-time and standalone systems.

Thus, the description is not intended to limit the invention and the configuration, operation, and behavior of the present invention has been described with the understanding that modifications and variations of the embodiments are possible, given the level of detail present herein. Accordingly, the preceding detailed description is not mean or intended to, in any way, limit the invention—rather the scope of the invention is defined by the appended claims.

What is claimed:

1. A method of processing a wafer comprising:
    aligning a reference wafer in a first metrology tool, the reference wafer having a first target structure at a first site;
    obtaining a first set of measured diffraction signals, each measured diffraction signal being measured from the first site on the reference wafer using a first set of sensor pixels in a first sensor;
    performing a first noise-reduction procedure to generate first noise-reduced data for the first sensor based on the first set of measured diffraction signals, the first noise-reduced data having first accuracy data associated therewith;
    obtaining simulation data for the reference wafer, the simulation data having simulated accuracy data associated therewith;
    identifying the first target structure using the first noise-reduced data when the first accuracy data is more accurate than the simulated accuracy data; and
    identifying the first target structure using the simulation data when the first accuracy data is not more accurate than the simulated accuracy data.

2. The method of claim 1, wherein performing the first noise-reduction procedure comprises:
    selecting a first number of sensor pixels;
    defining first signals at the first number of sensor pixels using a basis function, wherein each first signal is defined as:

$$s(i)=a(i)\cdot b(i,p)+r(i)+n(i)$$

wherein a(i) and p are parameters to be determined, b(i, p) is a pre-selected basis function, r(i) is a residual signal from the basis function, and n(i) is a noise signal to be suppressed.

3. The method of claim 2, wherein the basis function is defined using a polynomial and the polynomial is:

$$b(i,p)=p(0)+p(1)\cdot i+p(2)\cdot i^2+\ldots$$

4. The method of claim 2, wherein the parameters a(i) and p are selected so that the basis function is substantially close to a measured diffraction signal, and r(i) is minimized.

5. The method of claim 4, wherein r(i) is minimized using a regression method wherein one or more parameters of the basis function are adjusted.

6. The method of claim 5, wherein the regression method is performed at a center pixel.

7. The method of claim 1, wherein the first noise-reduction procedure is performed in real time.

8. The method of claim 1, wherein the first noise-reduction procedure is performed using Optical Digital Profilometry (ODP) procedures, spectral resolution averaging procedures, Moving Box averaging procedures, or Frequency filtering procedures, or any combination thereof.

9. The method of claim 1, further comprising:
    identifying the first noise-reduced data as low risk data and storing the first noise-reduced data, when the first accuracy data is more accurate than the simulated accuracy data; and
    performing a first corrective action, when the first accuracy data is not more accurate than the simulated accuracy data.

10. The method of claim 9, wherein the first corrective action includes selecting a new site, re-aligning the reference wafer, selecting a new limit, selecting a new noise-reduction procedure, selecting a new wafer, selecting a new set of pixels, selecting a new sensor, or selecting a new metrology tool, or any combination thereof.

11. The method of claim 1, further comprising:
    creating a noise-reduced (N-R) metrology model for the first target structure, the N-R metrology model comprising one or more enhanced profile parameters, one or more enhanced process parameters, and a noise-reduction procedure, wherein a noise component is minimized to improve accuracy for the enhanced profile parameters, or the enhanced process parameters, or a combination thereof; and
    storing the N-R metrology model.

12. The method of claim 1, further comprising:
    changing an angle of incidence, an intensity, a wavelength, a pixel pattern, or a number of pixels, or any combination thereof; and
    obtaining a second set of measured diffraction signals.

13. The method of claim 1, further comprising:
    identifying the reference wafer and wafers associated with the reference wafer as low risk wafers and storing the first noise-reduced data, when the first accuracy data is more accurate than the simulated accuracy data; and performing a first corrective action, when the first accuracy data is not more accurate than the simulated accuracy data.

14. The method of claim 1, further comprising:

identifying the reference wafer and wafers associated with the reference wafer as low risk wafers and storing the first noise-reduced data, when the first noise-reduced data is more accurate than the simulation data in a first set of wavelengths; and performing a first corrective action, when the first noise-reduced data is not more accurate than the simulation data in the first set of wavelengths.

15. The method as claimed in claim 1, wherein the first target structure is associated with a gate structure, a drain structure, a source structure, a two-dimensional transistor structure, a three-dimensional transistor structure a capacitor structure, a via structure, a trench structure, a two-dimensional memory structure, a three-dimensional memory structure, a sidewall angle, a critical dimension (CD), an array, a periodic structure, an alignment feature, a doping feature, a strain feature, a damaged-structure, or a sensor-related reference structure, or any combination thereof.

16. A system for using Noise-Reduced (N-R) data to examine a semiconductor wafer, the system comprising:

a wafer alignment means configured for aligning a reference wafer in a first metrology tool, the reference wafer having a first target structure at a first site, the wafer alignment means comprising a platform subsystem, an alignment subsystem coupled to the platform subsystem, and an alignment sensor coupled to the alignment subsystem;

one or more collection subsystems configured for obtaining a first set of measured diffraction signals, each measured diffraction signal being measured from the first site on the reference wafer using a first set of sensor pixels in a first sensor; and a controller configured for performing a first noise-reduction procedure to generate first noise-reduced data for the first sensor based on the first set of measured diffraction signals, the first noise-reduced data having first accuracy data associated therewith, for obtaining simulation data for the reference wafer, the simulation data having simulated accuracy data associated therewith, for identifying the first target structure using the first noise-reduced data when the first accuracy data is more accurate than the simulated accuracy data, and for identifying the first target structure using the simulation data when the first accuracy data is not more accurate than the simulated accuracy data.

17. The system of claim 16, wherein the controller is further configured for selecting a first number of sensor pixels, for defining first signals at the first number of sensor pixels using a basis function, wherein each first signal is defined as:

$$s(i)=a(i) \cdot b(i,p)+r(i)+n(i)$$

wherein a(i) and p are parameters to be determined, b(i, p) is a pre-selected basis function, r(i) is a residual signal from the basis function, and n(i) is a noise signal to be suppressed.

18. The system of claim 17, wherein the controller is further configured for defining the basis function using a polynomial, wherein the polynomial is:

$$b(i,p)=p(0)+p(1) \cdot i+p(2) \cdot i^2+\ldots$$

19. A non-transitory computer-readable medium containing computer-executable instructions for performing a Noise-Reduction (N-R) procedure, the method comprising instructions for:

aligning a reference wafer in a first metrology tool, the reference wafer comprising a first target structure at a first site;

obtaining a first set of measured diffraction signals, each measured diffraction signal being measured from the first site on the reference wafer using a first set of sensor pixels in a first sensor;

performing a first noise-reduction procedure to generate first noise-reduced data for the first sensor based on the first set of measured diffraction signals, the first noise-reduced data having first accuracy data associated therewith;

obtaining simulation data for the reference wafer, the simulation data having simulated accuracy data associated therewith;

identifying the first target structure using the first noise-reduced data when the first accuracy data is more accurate than the simulated accuracy data; and identifying the first target structure using the simulation data when the first accuracy data is not more accurate than the simulated accuracy data.

* * * * *